United States Patent
Belykh et al.

(10) Patent No.: US 7,050,618 B2
(45) Date of Patent: May 23, 2006

(54) METHOD FOR ANTISCATTER STATIONARY GRID ARTIFACTS DETECTION AND ATTENUATION IN DIGITAL RADIOGRAPHIC IMAGES

(75) Inventors: Igor N. Belykh, Palo Alto, CA (US); Craig W. Cornelius, Menlo Park, CA (US)

(73) Assignee: Eastman Kodak Company, Rochester, NY (US)

( * ) Notice: Subject to any disclaimer, the term of this patent is extended or adjusted under 35 U.S.C. 154(b) by 597 days.

(21) Appl. No.: 10/068,930

(22) Filed: Feb. 8, 2002

(65) Prior Publication Data
US 2003/0152259 A1  Aug. 14, 2003

(51) Int. Cl.
*G06K 9/00* (2006.01)

(52) U.S. Cl. ............... 382/132; 382/278; 382/275; 382/261

(58) Field of Classification Search ........ 382/128–134, 382/260–265, 268, 269, 274, 275, 277–283; 345/611; 378/62, 164
See application file for complete search history.

(56) References Cited

U.S. PATENT DOCUMENTS

| | | | |
|---|---|---|---|
| 1,164,987 A | 12/1915 | Bucky | |
| 4,792,900 A | 12/1988 | Sones et al. | |
| 5,276,614 A * | 1/1994 | Heuscher | 382/260 |
| 5,440,647 A | 8/1995 | Floyd et al. | |
| 5,661,818 A | 8/1997 | Gaborski et al. | |
| 5,881,162 A * | 3/1999 | Ishimitsu | 382/132 |
| 6,233,060 B1 * | 5/2001 | Shu et al. | 358/1.9 |
| 6,269,176 B1 | 7/2001 | Barski et al. | |
| 6,333,990 B1 * | 12/2001 | Yazici et al. | 382/132 |
| 6,587,594 B1 * | 7/2003 | Yamada | 382/260 |

OTHER PUBLICATIONS

Text Book: Introduction to Statistical Time Series, 2nd edition, W. A. Fuller, Wiley, John & Sons Incorporated, 1995, pp. 7-17, 313-315, 338-349.

(Continued)

*Primary Examiner*—Joseph Mancuso
*Assistant Examiner*—Craig Kronenthal
(74) *Attorney, Agent, or Firm*—Susan L. Parulski

(57) ABSTRACT

A method for detecting and attenuating grid artifacts in a digital radiographic image comprising; providing an input digital radiographic image; processing the input digital radiographic image with a detection algorithm based on 2-D dynamic correlation in both spatial and frequency domains to determine whether the input digital radiographic image has a grid artifacts; and if it does detecting the grid orientation, frequency, and signal-to-noise ratio of the grid artifacts, designing a frequency bandstop (notch) digital 1-D filter as a function of the grid frequency and attenuation level; and suppressing the grid artifacts by further processing said input digital radiographic image with said designed filter to produce an output digital radiographic image of improved image quality.

9 Claims, 8 Drawing Sheets

OTHER PUBLICATIONS

Text Book: Digital Filters, R. W. Hamming, Englewood Cliffs, New Jersey: Prentice-Hall, 1985, pp. 109-119, 136-141, 233-239, 167-187.

Text Book: Intel Signal Processing Library, Reference Manual, v. 4.5 Intel, 2000.

Text Book: Digital signal processing, A. V. Oppenheim, R. W. Schafer, Englewood Cliffs, New Jersey, Prentice-Hall, 1975, pp. 113-115.

Text Book: Compilation of time windows and time shapes for Fourier analysis, R. W. Potter, 02-5952-0705, Hewlett-Packard, 1971, pp. 100, 110, 200, 201, 210, 301, 310, 311, 330.

Text Book: Digital Image Processing, K. W. Pratt, 2, sup. nd. edition, John Wiley & Sons, Incorporated, 1991, pp. 171-191.

* cited by examiner

METHOD FOR ANTISCATTER STATIONARY GRID ARTIFACTS DETECTION AND ATTENUATION IN DIGITAL RADIOGRAPHIC IMAGES

FIELD OF THE INVENTION

This invention relates in general to digital medical imaging, and specifically to the presentation of digital projection radiography images for improved image quality and elimination of grid artifacts.

BACKGROUND OF THE INVENTION

In projection radiography the detected radiation field contains both primary and secondary (scattered) components. Scattered X-rays reduce the contrast of images. Antiscatter grids absorb scattered radiation and increase image contrast. Devices that hold grids and X-ray film are known as "Bucky" from the name of Gustav Bucky, who first designed stationary grids in 1913 in Germany, and patented them in the USA, U.S. Pat. No. 1,164,987, issued Dec. 21, 1915. At the present time both stationary and moving grids are used for this purpose. The disadvantage of stationary grids is that they create line artifacts on film and digital images and, when changed in size for display or reprinting, create visible Moiré patterns due to spatial aliasing. Moving grids effectively remove the stripe artifacts by means of temporal blur of the various stationary grid designs, including parallel, focused, and crossed, the most commonly used are linear grids with parallel stripes in one direction. Crossed grids have grid stripes in both orthogonal directions and are used less frequently. The most important features of a linear grid are its resolution in line/mm (millimeter) and the ratio between grid stripes height and distance. Due to the spatial regularity of the grids in one direction, strengthened by geometrical cut-off effect, the stripe artifacts in digital radiographic images can be considered as 1-D coherent spatial noise of a frequency corresponding to the distance between stripes.

In U.S. Pat. No. 5,661,818, issued Aug. 26, 1997, inventors Gaborski et. al., discloses a grid artifacts detection method which is based on a double auto-correlation calculation. Variances are measured independently, both horizontally and vertically and a statistical F test is performed to determine if the variances are the same over a randomly chosen sampling of locations within the image. Votes are then tallied and if a majority indicates that the variances are different, a decision is made in favor of a grid being present. This method, however, does not provide a key parameter— the grid line frequency—as well as other important grid features that might be useful in further suppression. Another method was proposed in U.S. Pat. No. 6,269,176, issued Jul. 31, 2001, inventors Barski et al. It is based on 1-D spectral approach and comprises several steps: finding a window for analysis, obtaining averaged 1-D Fourier power spectra in each direction, searching for the maxima in the right part of smoothed and morphologically filtered averaged spectra as grid peak candidates, collecting the attributes of each peak, sorting the candidates in terms of figure-of-merit (FOM), and picking the best candidate with the highest FOM. This method provides such grid peak attributes as orientation, frequency, magnitude, total energy, half-width of full maximum, coherency. Although these methods were suitable for the uses for which they were intended, the main disadvantage of both of these methods is the uncertainty in picking the right candidate if several frequencies are detected, due to the lack of dynamic tracking of success in the 1-D analysis. A second disadvantage is that neither method provides information about signal-to-noise ratio (SNR) in the frequency grid peak area, which is needed as a parameter for further automatic tuning and design of the attenuation filter.

In the present invention a method for grid linear artifact detection is proposed based on 2-D dynamic correlation in both spatial and frequency domains. This method provides results including grid orientation, frequency, and SNR.

A 1-D frequency bandstop (notch) filter is known as the best instrument for narrow-banded noise elimination. Several different algorithms for notch filter design and implementation are known (see: Hamming R. W. "Digital filters", Englewood Cliffs, N.J.: Prentice-Hall, 1985). In order to maximize the suppression of grid artifacts and to minimize image distortion, there are several filter transfer function parameters to tune, including cut frequency, bandwidth, attenuation level, and Gibbs event amplitudes.

The grid artifact suppression method proposed in U.S. Pat. No. 6,269,176, issued Jul. 31, 2001, inventors Barski et al., was based on 1-D adaptive gaussian blur filters design for use in the spatial domain. The principal disadvantage of that method is that Fourier transform of a gaussian filter is just a transfer function of a lowpass filter. It is very complicated to tune such a filter to the right cut frequency, i.e. grid peak frequency, and to compute this filter coefficients in the spatial domain. Moreover, the disadvantage of lowpass filter vs. a bandstop filter is that all frequencies, higher than the one identified as the grid frequency in each specific gaussian filter are eliminated. This is the reason that such filters cause image blur, which in many cases may be unacceptable from a clinical point of view.

In the present invention a method of 1-D frequency bandstop filter is proposed as the method that best corresponds to the noise nature of the grid artifact, for the purpose of removing both grid line artifacts and Moiré patterns, which are very noticeable when a softcopy image display is resized. There were no prior efforts found in the patent record to use a frequency notch filter to suppress grid artifacts.

SUMMARY OF THE INVENTION

According to the present invention, there is provided a solution to the problems discussed above.

According to a feature of the present invention, there is provided a method for grid line artifacts and Moiré patterns detection and suppression in digital radiographic images. A detection algorithm is based on a dynamic analysis of autocorrelation and cross-correlation functions $1^{st}$ derivative spectra calculated in a defined square region within the image in each of two dimensions. It provides grid frequency, SNR and orientation. A digital 1-D frequency bandstop filter is automatically designed as a function of detected grid frequency and SNR. This filter is then applied to the input image in the direction orthogonal to the detected grid orientation.

ADVANTAGEOUS EFFECT OF THE INVENTION

The invention has the following advantages.

1. The detection algorithm is more reliable in grid peak candidate estimation because of using second dimension for analysis with a measure of robustness.

2. The detection algorithm provides grid SNR along with frequency and orientation, i.e. a set of parameters necessary and sufficient to automatically design and apply the attenuation filter.

3. The frequency bandstop filter eliminates either grid line artifacts on magnified images and Moiré patterns on minified images without introducing clinically important blur.

4. The method of the invention provides improved digital radiography image quality.

DETAILED DESCRIPTION OF THE INVENTION

Figure 10:
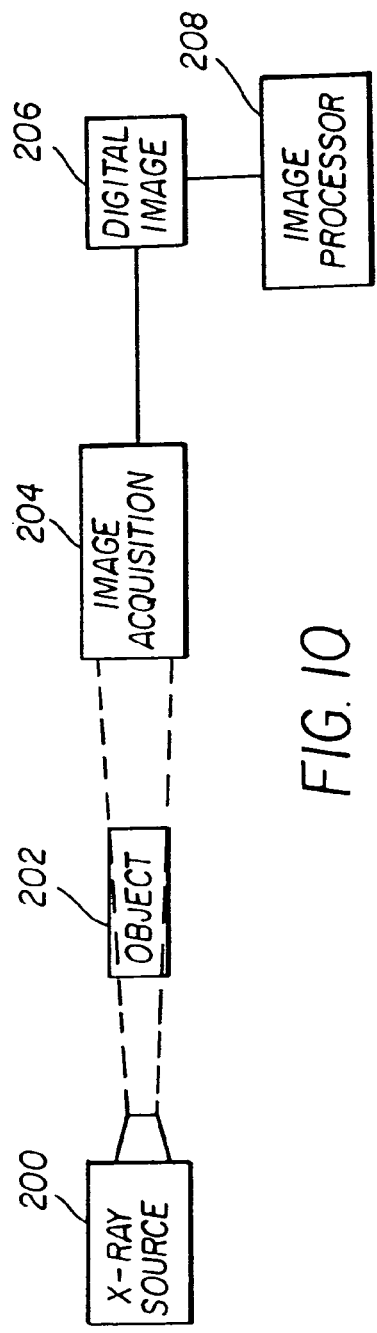
FIG. 10 is a block diagram of a digital radiographic image acquisition system.

The method of the present invention is described as a series of operations performed on a digital image, such as a digital radiographic image of a body part. The digital image can be formed by the digital image acquisition system of FIG. 10. As shown, x-ray source 200 projects x-rays through object 202 (such as a body part extremity, e.g., hand or foot) to image acquisition system 204. The image acquisition system can be, for example, (1) a standard x-ray screen/film combination which produces an x-ray film image which is processed chemically or thermally and the processed film digitized by a scanner/digitizer 206; (2) a computed radiography system where a latent x-ray image is formed in a storage phosphor 204 and a corresponding digital image is produced by reading out the storage phosphor by a CR reader 206; (3) a diagnostic scanner (such as MRI, CT, US, PET) produces an electronic x-ray image which is digitized, and (4) a direct digital acquisition system typically consisting of a phosphor based scintillating screen coupled to an imager (CCD, MOS) through a lens or fiber optic system.

Figure 11:
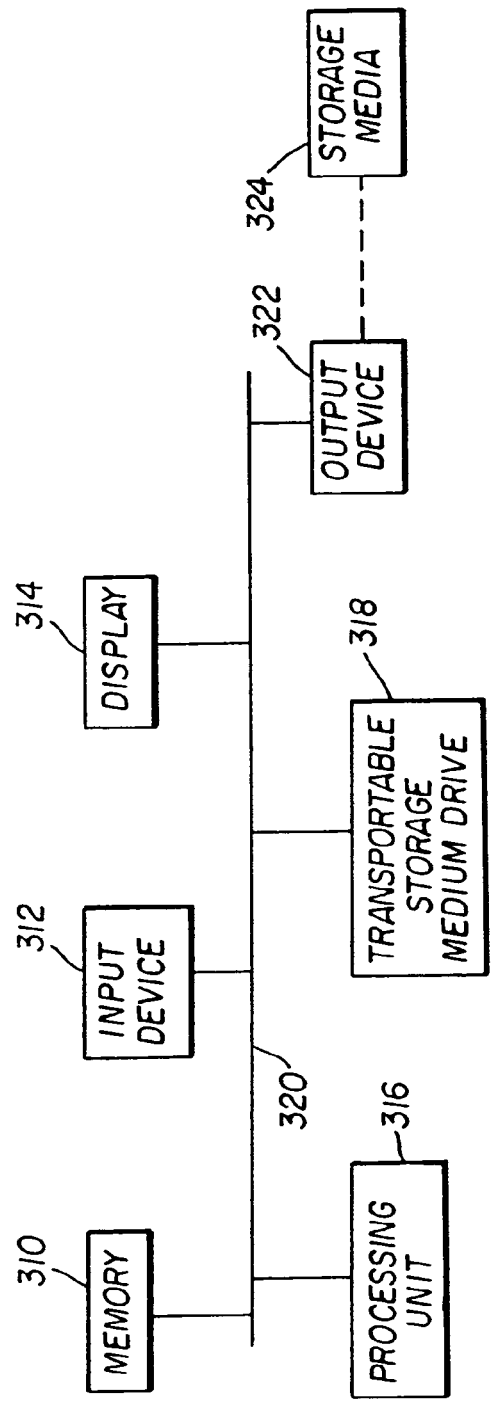
FIG. 11 is a block diagram of a digital processor for carrying out the method of the present invention.

The digital image is processed in image processor 208, according to the method of the present invention. Image processor 208 can take the form of a digital computer, such as illustrated in FIG. 11. In such case, one or more of the steps of said method can be carried out using software routines. Image processor 208 can also include hardware or firmware for carrying out one or more of said method steps. Thus, the steps of the method of the invention can be carried out using software, firmware, and hardware, either alone or in any preferable combination.

As shown in FIG. 11, a digital computer 300 includes a memory 310 for storing digital images, application programs, operating system, etc. Memory 310 can include mass memory (such as a hard magnetic disc or CD ROM), and fast memory (such as RAM). Computer 300 also includes input device 312 (such as a keyboard, mouse, touch screen), display 314 (CRT monitor, LCD), central processing unit 316 (microprocessor), output device 318 (thermal printer, dot matrix printer, laser printer, ink jet printer). Components 310, 312, 314, 316, 318 are connected together by control/data bus 320. Computer 300 can include a transportable storage medium drive 322 for reading from and/or writing to transportable storage media 324, such as a floppy magnetic disk or writeable optical compact disk (CD).

As used in this application, computer readable storage medium can include, specifically, memory 310 and transportable storage medium 324. More generally, computer storage medium may comprise, for example, magnetic storage media, such as magnetic disk (hard drive, floppy disk) or magnetic tape; optical storage media, such as optical disk, optical tape, or machine readable bar code; solid state electronic storage devices, such as random access memory (RAM), read only memory (ROM); or any other physical device or medium which can be employed to store a computer program.

The present invention provides a method for improving projection radiographic images which contain stationary grids. The present invention includes a method of detecting the grids that can be used alone or in combination with a method of suppressing the grids from the radiographic image to improve image quality. The detecting and suppressing method of the present invention can be applied more broadly to detect a pattern of lines in a digital image and to suppress a detected pattern of lines to improve image quality.

Figure 9:
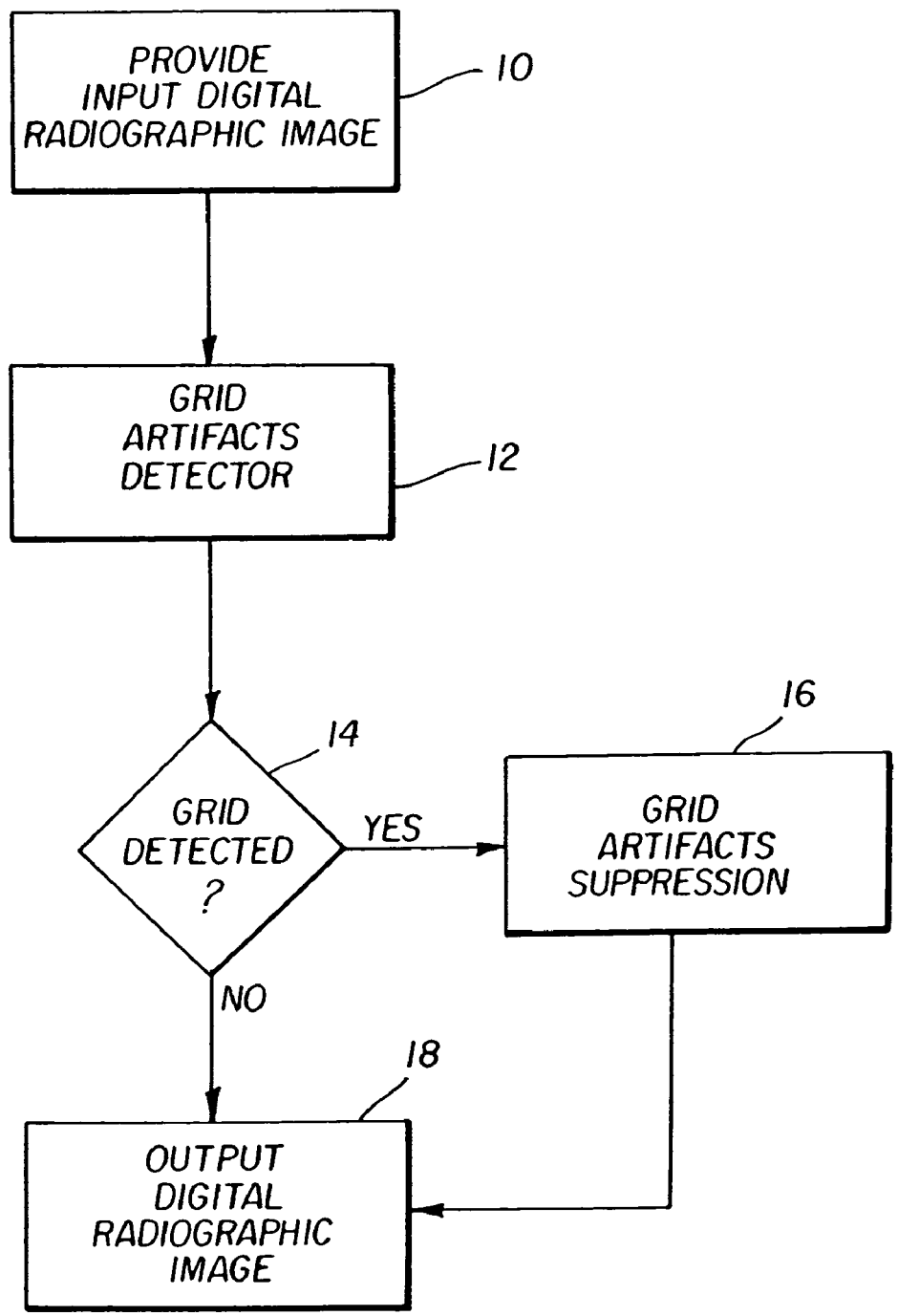
FIG. 9 is a block diagram of an embodiment of the present invention.

FIG. 9 is a block diagram of the general method of the present invention: an input digital radiographic image is provided (box 10). The image is processed with the grid artifacts detecting algorithm (box 12) to detect a grid in the image (diamond 14). If a grid is detected, the grid artifacts are suppressed by processing the image with the grid suppression algorithm of the invention (box 16). A grid suppressed output digital radiographic image is thereby produced (box 18). If no grid is detected, (diamond 14) the output image (box 18) is the same as the input image (box 10).

The method of FIG. 9 can be applied more broadly to any digital image which can have a pattern of lines. In such application, a digital image would be provided (box 10), the line detection algorithm would be applied to the input digital image to detect a pattern of lines in the input image (diamond 14). If it is desired to suppress the pattern of lines, if detected, the line suppression algorithm is applied to the input image (box 16) to produce an output digital image free of the lines (box 18).

Figure 1:
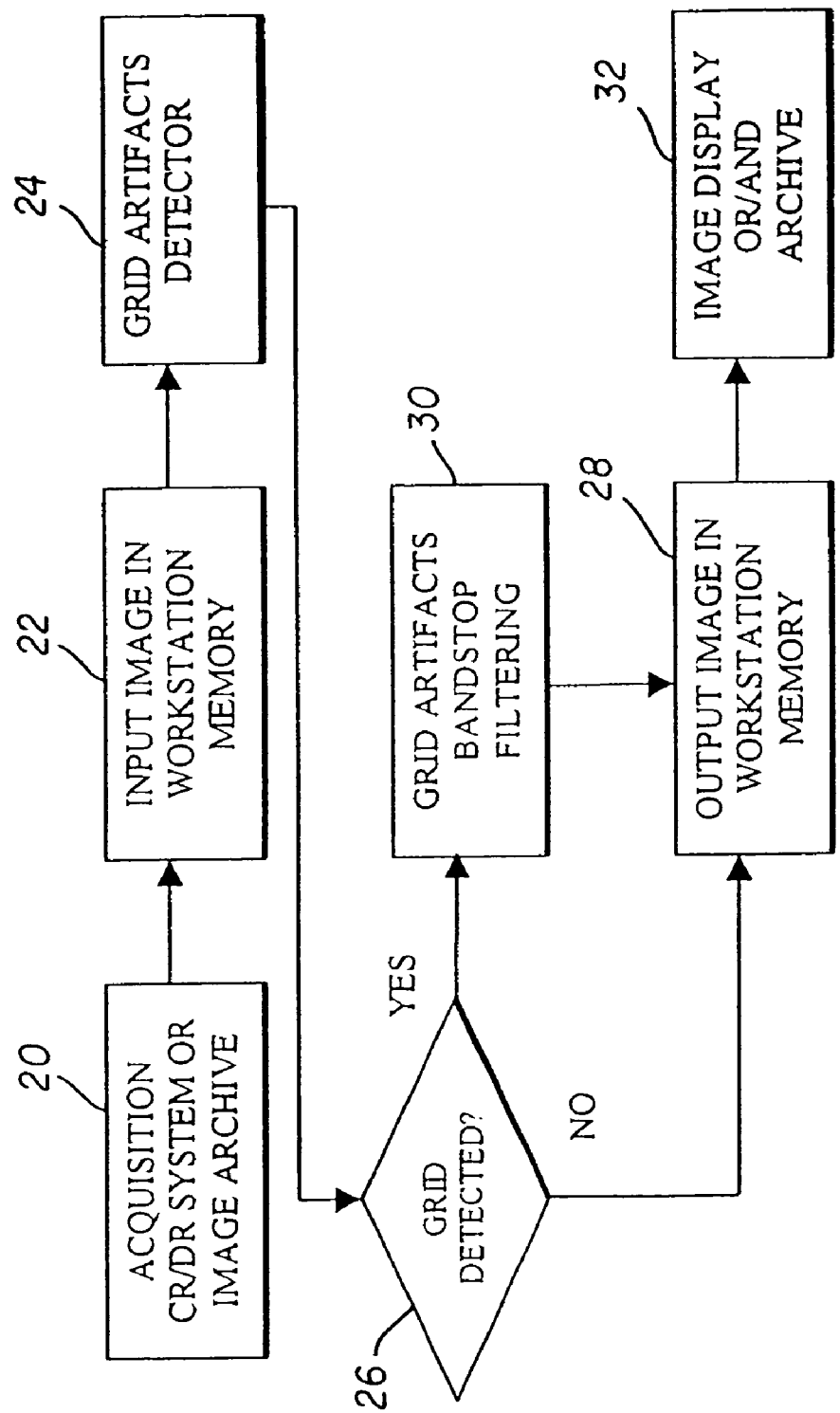
FIG. 1 is a block diagram illustrating the process flow for image input, processing, and output, including the proposed grid artifacts attenuation method.

In general, method of the present invention comprises two main algorithms—detection and attenuation—and each of them consists of sequence of operations performed on digital radiographic images to detect and to eliminate grid artifacts (see block diagram in FIG. 1). As soon as an image is captured in CR or DR system, digitized from a film, or retrieved from an image archive (box 20), it is stored in workstation memory (box 22). Then the image is analyzed by a grid detector algorithm (box 24). If no grid is detected (diamond 26), no grid suppression image processing is applied, and the output image (box 29) will be the same as input one. If a grid is detected (diamond 26), then 1-D grid artifact suppression is performed in the direction orthogonal to the detected grid orientation (box 30), and the output image (box 28) is the result of the image processing. Finally, the output image may be displayed, printed to film or paper or other media, transmitted to another computer system, or stored in a digital archive (box 32).

Figure 2:
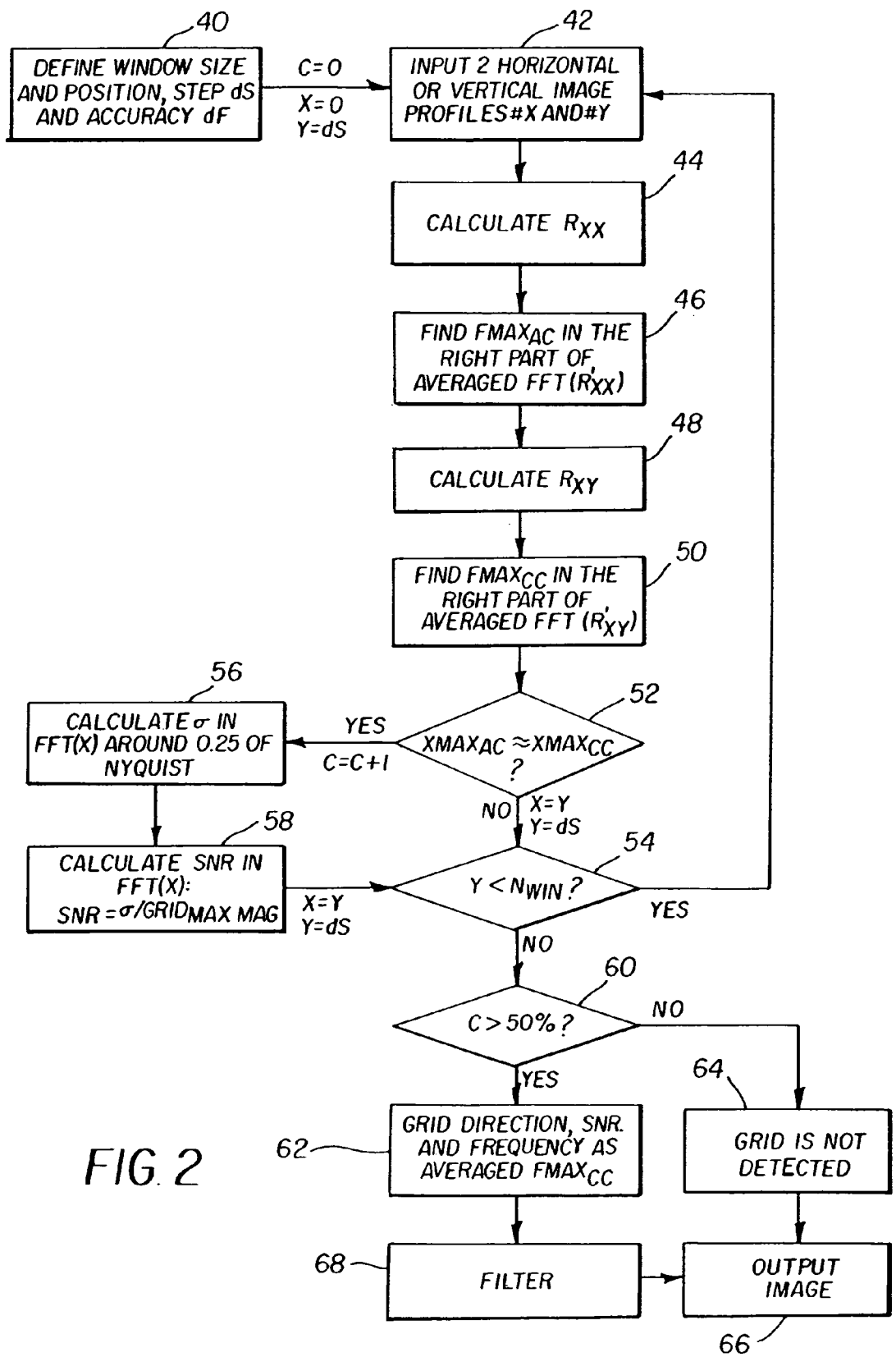
FIG. 2 is a block diagram illustrating the proposed grid linear artifact detection algorithm.

The grid detection algorithm proposed in the present invention consists of several steps (see block diagram in FIG. 2). The predefined numbers for analysis are: the size and location of a square region of the image in the spatial pixel domain (called "window" below), the increment step dS as a profile number, and the required grid peak search accuracy dF in the frequency domain. Linear window size (LWS) is defined as a power of 2 nearest to the half of smallest image size known as width and height. The window may be positioned in any of the 4 image corners, beginning from the image edges, where grid artifacts are usually strengthened by the geometrical cut-off effect. The step dS=1% of LWS. The accuracy dF=1% of Nyquist frequency. Then a loop is initiated for each of the horizontal and vertical directions sequentially for a number of profiles $N_{win}$ in the defined window with increment dS. The loop comprises several operations:

1. Set initial values for profile numbers X=0, Y=dS, and detection success counter C=0 (box 40);

2. Input 2 image profiles #X and #Y (box 42);

3. Calculate an auto-correlation function for the profile X, take its $1^{st}$ derivative, find maximum $FMAX_{AC}$ in the right part of its averaged Fourier power spectrum (high frequency), and store $FMAX_{AC}$ frequency (box 44, box 46);

4. Calculate a cross-correlation function for the X and Y profiles, take its $1^{st}$ derivative, find maximum $FMAX_{CC}$ in the right part of its averaged Fourier power spectrum, and store $FMAX_{CC}$ frequency (box 48, box 50);

5. Compare if $FMAX_{AC} \approx FAMX_{CC}$ with accuracy dF (diamond 52); if they are not equal then increment profile numbers X=Y, Y=Y+dS and go to step 8 (diamond 54); if they are equal then increment a detection success counter C=C+1 and go to step 6 (box 56);

6. Obtain amplitude Fourier spectrum of profile X, then calculate a standard deviation σ of the signal frequencies within the bandwidth equal to accuracy dF at the frequency of 0.25 Nyquist (box 56);

7. Calculate signal-to-grid SNR as a ratio of σ and grid maximum magnitude detected within the bandwidth equal to accuracy dF at the frequency of $FMAX_{CC}$, then store accumulated SNR value, and increment profile numbers X=Y, Y=Y+dS);

8. Check if Y does not exceed Nwin (diamond 54) then go to step 2 (box 42) else go to step 9 (diamond 60);

9. Check if detection success counter C exceeds 50% of total analyzed profiles number (diamond 60). If so, then go to step 11 (box 62) else go to step 10 (box 64);

10. Since a grid is not detected (box 64), the output image (box 66) is the same as input;

11. Since grid is detected in this direction obtain grid frequency as averaged frequency of $FMAX_{CC}$ matched with $FMAX_{AC}$, and obtain averaged SNR value (box 62);

12. Perform the grid filtering operation on the image (below) (box 68).

The described grid artifact detection algorithm provides grid orientation, frequency and SNR as a set of parameters necessary and sufficient for the automatic design of a frequency notch filter algorithm which is used for artifact suppression, also proposed in the present invention.

The statistical and spectral fundamentals of the proposed detection algorithm are the following. The human eyes and brain correlate spatial patterns simultaneously in each of the two spatial dimensions. The image profiles can be considered as an ensemble of realizations of a stochastic process. The auto-correlation function (ACF) and its spectrum characterize periodic processes in 1-D. The ACF has the same frequency spectrum but more smoothed one compare to the image profile spectrum. The cross-correlation function (CCF) and its frequency spectrum of 2 image profiles characterize the relation between them in the direction orthogonal to ACF. CCF has more smoothed spectrum similar to ACF for stationary processes with a coherent noise. Matching the ACF and CCF frequency peaks reveals the presence of 1-D spatial noise. Therefore, the combination of such statistical spatial and frequency analysis gives a 2-D correlation. Dynamic tracking of detection success is the measure of algorithm robustness and is close to 100% in the presence of the grid and is close to 0% else, as tested. The intermediate computation of ACF and CCF $1^{st}$ derivatives described in steps 3 and 4 above helps to remove the influence of low frequency trends in frequency spectra of those functions. The numerical techniques at each of the steps above are well known (see: Fuller W. A. "Introduction to Statistical Time Series", 2nd Edition, Wiley, John & Sons, Incorporated, 1995).

Grid artifact attenuation algorithm proposed in the present invention comprises several procedures. If grid was detected and its orientation and frequency are known then a digital 1-D notch filter is designed as a function of grid frequency and attenuation level. Different algorithms for notch filter design and implementation are known (see: Hamming R. W. "Digital filters", Englewood Cliffs, N.J.: Prentice-Hall, 1985, pages 109–118). The goal here is to choose the filter that maximizes the suppression of grid artifacts with minimal image distortion. Both factors mentioned above depend on filter transfer function features such as attenuation level and Gibbs event amplitudes respectively. Attenuation level in its turn depends on filter operator length and bandwidth.

In the present invention the Potter finite impulse response trigonometric trapezoidal filter algorithm (see: Hamming R. W. "Digital filters", Englewood Cliffs, N.J.: Prentice-Hall, 1985, pages 136–140; and Potter R. W. "Compilation of time windows and time shapes for Fourier analysis", 02-5952-0705, Hewlett-Packard, 1971) is proposed as one of the best candidates for the optimal implementation of the notch filter transfer function. The notch filter coefficients are calculated from 2 lowpass filters coefficients tuned on low $f_1$ and high $f_2$ cut frequencies, which are obtained from grid frequency $f_g$ and bandstop width B using:

$$f_1 = f_g - B/2, \quad f_2 = f_g + B/2 \tag{1}$$

For each lowpass filter, rectangular filter transfer function coefficients are calculated using:

$$a_0 = \omega_n x, \quad a_{kn} = \sin(\omega_n x k)/\pi k, \quad k=1,2,\ldots,M; \quad n=1,2; \tag{2}$$

followed by trapezoid smoothing at the end using:

$$a_{Mn} = a_{Mn}/2,$$

where M is half of the filter symmetrical operator length and $\omega_n$ is one of the cut frequencies defined in (1), $\omega_n = 2\pi f_n$ are low cut frequencies, and x is the sampling rate. After that, a smoothing window is applied:

$$b_{kn} = a_{kn} p_k, \tag{3}$$

where $p_k$ are Potter P310 smoothing window coefficients calculated using:

$$p_k = c_k/c_0 [d_0 + 2 \Sigma_{(i)} (d_i \cos (\pi i k)/M)], \quad i=1, 2, 3; \quad (4)$$

where, $C_k = \frac{1}{2}$, if k=M, $C_k = 1$, if k≠M;

$C_0 = 2.8108034$;

$d_0 = 1$, $d_1 = 0.684988$, $d_2 = 0.202701$, $d_3 = 0.0177127$,

Then bandstop filter coefficients are calculated using:

$$bs_0 = 1 - b_{02} + b_{01}, \quad bs_k = b_{k2} - b_{k1} \quad (5)$$

Final notch filter operator coefficients are obtained by adding the left part coefficients symmetrical to the right ones calculated in (5) using:

$$bs_{-k} = bs_k \quad (6)$$

Attenuation levels can be adjusted using 2 filter parameters: half of the operator length in a range of 24–32 coefficients and rejection bandwidth in a range of 0.07–0.1 as a fraction of Nyquist frequency. Finally, attenuation steps can be designed as a user-selectable option within a range of about −20 dB to −60 dB with increment of −3 to −4 dB. Automatic selection of attenuation level is based on grid peak SNR revealed by the detector. The preferred (default) value can be set up manually for the appropriate attenuation of grid artifacts for a specific CR/DR modality image. Among other possible filter algorithm implementations are Chebysheb filter of type II, and Kaiser filter (see: Hamming R. W. "Digital filters", Englewood Cliffs, N.J.: Prentice-Hall, 1985, pages 167–187 and 233–238).

Figure 3:
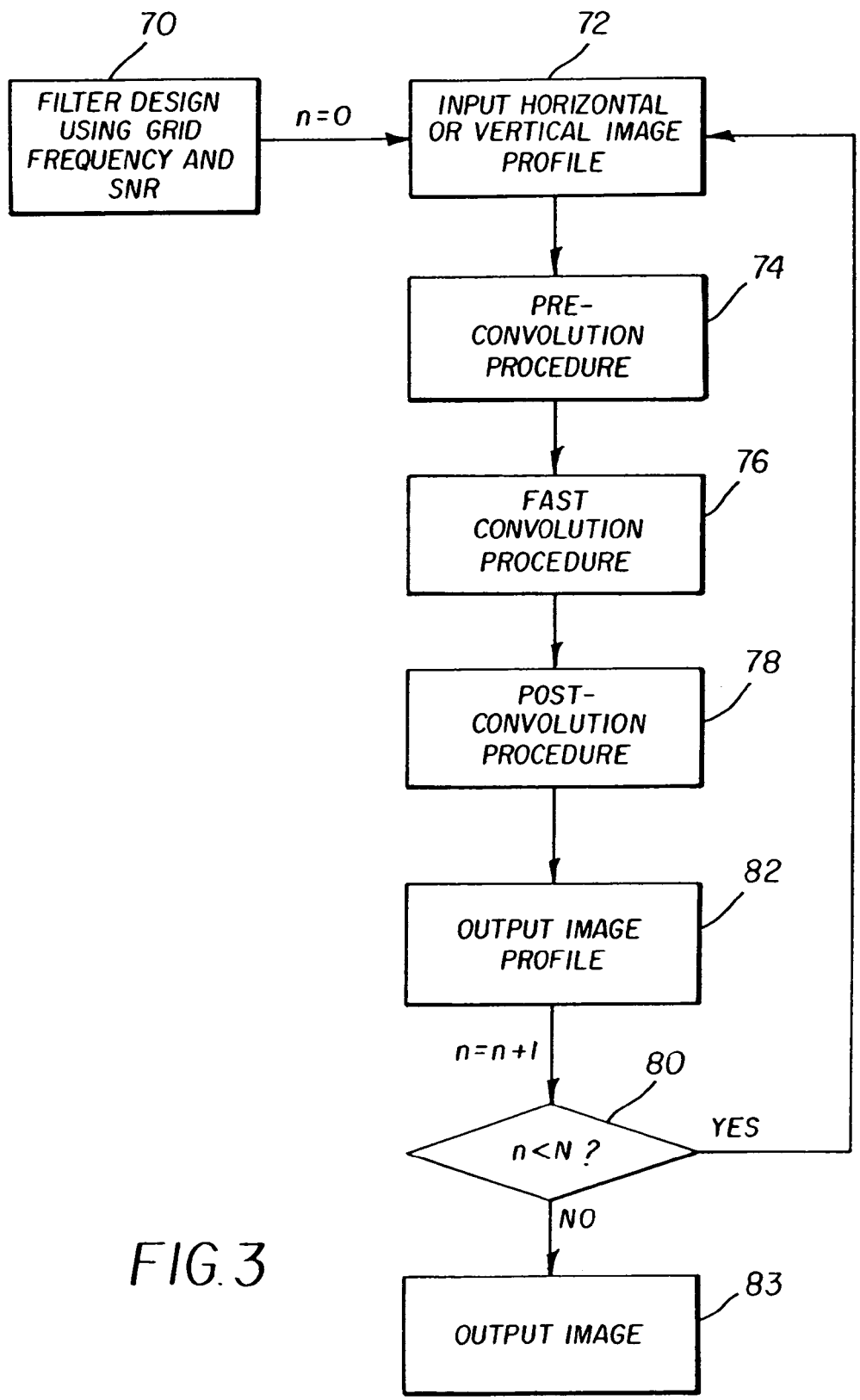
FIG. 3 is a block diagram illustrating the proposed grid artifacts filtering algorithm.

After digital filter is designed (FIG. 3, box 70), there is a loop for image profiles filtering: horizontal or vertical image profiles are input (box 72), pre-convolution, fast convolution, and post convolution procedures are applied (boxes 74, 76, 78) to each image profile to produce an output image profile (box 82). When all profiles n=N are processed (diamond 80), an output image 83 results. Filtering is based on 1-D spatial domain convolution of filter coefficients, with each of N horizontal or vertical (or both for crossed grids) image profile, depending on grid orientation and configuration. N is equal to total number of horizontal or vertical profiles in a specific image. The traditional method of convolution is well known in the art of digital image processing (see: Hamming R. W. "Digital filters", Englewood Cliffs, N.J.: Prentice-Hall, 1985; and William K. Pratt, "Digital Image Processing", John Wiley & Sons Inc, 1991, pages 171–191).

In this invention, a technique for the best convolution performance—the main time critical operation—is proposed based on known algorithms such as the "overlap-save convolution" algorithm (see: Oppenheim et al, "Digital Signal Processing", Prentice-Hall, Inc. 1975, pages 113–115). This is generally possible with any computer platform, or may also be implemented using low-level vector algebra and math functions libraries for specific computer platforms such as Intel Signal Processing Library (see: Intel SPL, 2000) for Intel based computers. Using the proposed techniques the convolution performance can be improved by 4 to 10 times or more compare to a conventional convolution approach.

Figure 4:
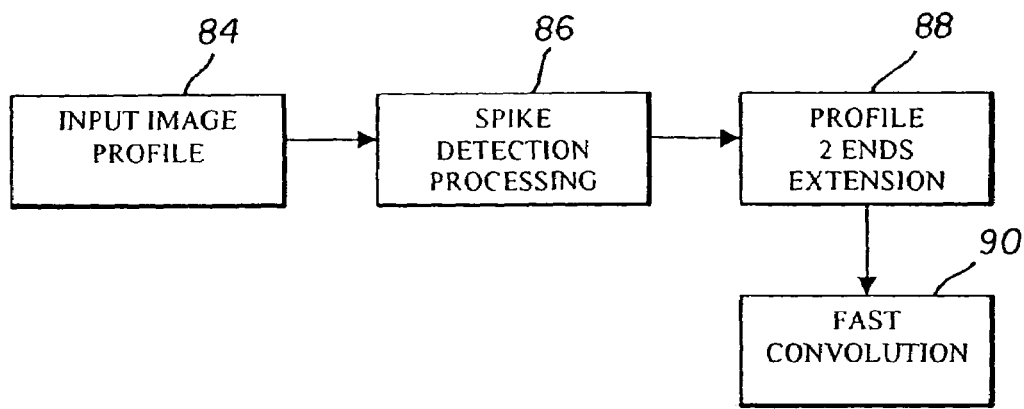
FIG. 4 is a block diagram illustrating the pre-convolution procedure steps.

In this invention a pre-convolution and post-convolution procedures (FIG. 3, boxes 74, 78) are proposed for filter edge and spikes effects elimination. Edge effect is visible line artifact with a length of M equal to half of filter operator length caused by its convolution with a number of pixel values containing big and sharp change in intensity of one sign or simply the end of pixel series at image edge. Spike effect is a noticeable line artifact caused by filter weights convolution with extremely high and narrow peak in intensity. Those spikes might be originated by bad pixels in CR/DR screens/detectors or by possible their damage. A pre-convolution procedure (see: block diagram in FIG. 4) consists of 2 main steps. At first step each input (box 84) image profile is extended at its both ends (box 88) by replicating M times first and last profile value respectively, for filter edge effect elimination purpose. At second step each image profile is analyzed by spike detection and processing function (box 86). Fast convolution is then effected (box 90).

The spike detection algorithm proposed in the present invention performs spike detection, retaining the values of detected spikes, and substituting the values of such spikes with linearly interpolated neighbor values. Spikes detection is based on statistical thresholding approach. An input image profile is considered as a smooth continuous function defined on the image profile interval except for some pre-defined number of values at image edges. The spike detection threshold is defined as a mean square value of the first derivative of that function. The values of a differentiated profile are compared with a calculated threshold. If they exceed it and are 3 or fewer pixels wide, the corresponding intensity values in the image profile are treated as spikes. Then spike values and positions are stored in a memory buffer, and their values are substituted with linear interpolated neighbor values.

Figure 5:
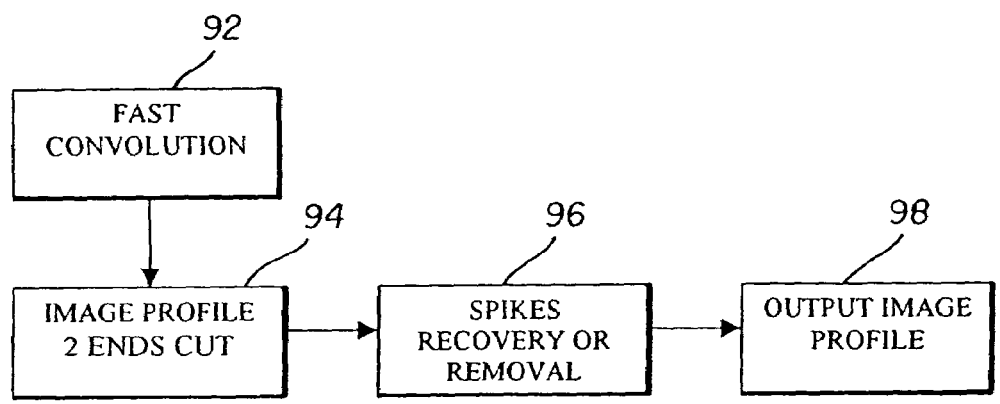
FIG. 5 is a block diagram illustrating the post-convolution procedure steps.

A post-convolution procedure comprises 2 steps with the inverse functions of the pre-convolution procedure functions (see: block diagram in FIG. 5). In the first step after fast convolution has been effected (box 92), both ends of each extended filtered profile are removed to extract the profile with original length (box 94). In the second step the memorized spikes are returned back to their original positions if they are considered clinically valuable. If not, they are not restored, i.e. they are eliminated (box 96). The latter choice might be useful for low quality images containing a lot of bright dots or scratches. The edge effect elimination is a mandatory function while spike processing function is optional defined by user. The output image profile results (box 98). The method to determine if the spikes should be restored is not specified by this invention.

When all image profiles have been filtered, the output image is stored in workstation memory (see: block diagram in FIG. 1). After that the image might be displayed, printed, transmitted, and/or stored in image archive.

Figure 6A:
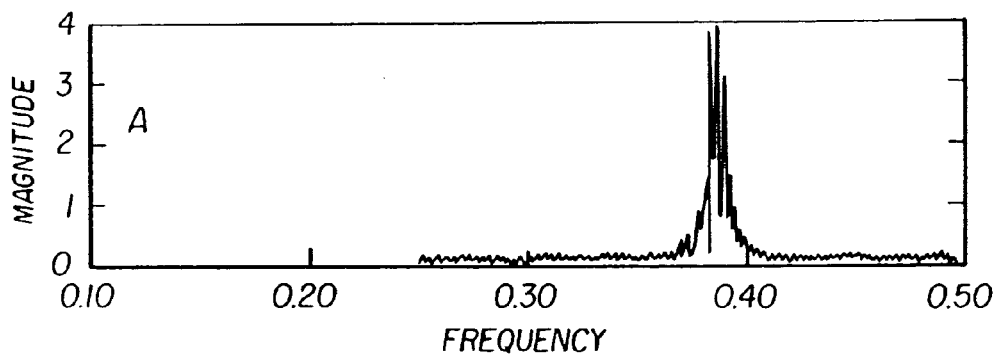
FIGS. 6A–6C illustrate averaged Fourier spectra of: A—CR image profile, containing grid peak; B—$1^{st}$ derivative of the autocorrelation function; C—$1^{st}$ derivative of the cross-correlation function.
Figure 6B:
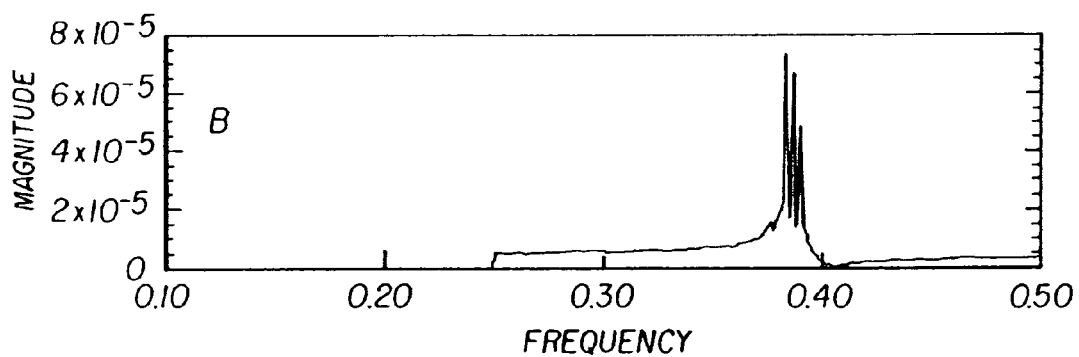
Figure 6C:
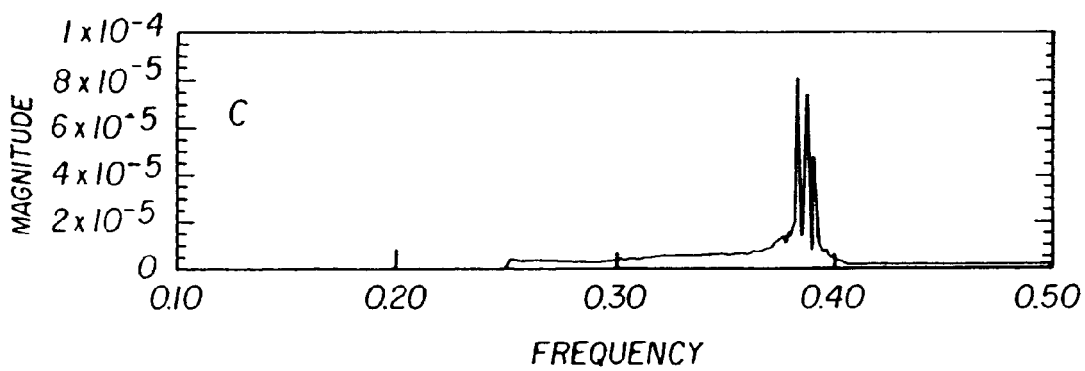

FIGS. 6A–6C illustrate respective averaged Fourier spectra of a CR image profile, containing grid peaks;

$1^{st}$ derivative of the auto-correlation function; and $1^{st}$ derivative of the cross-correlation function.

Figure 7A:
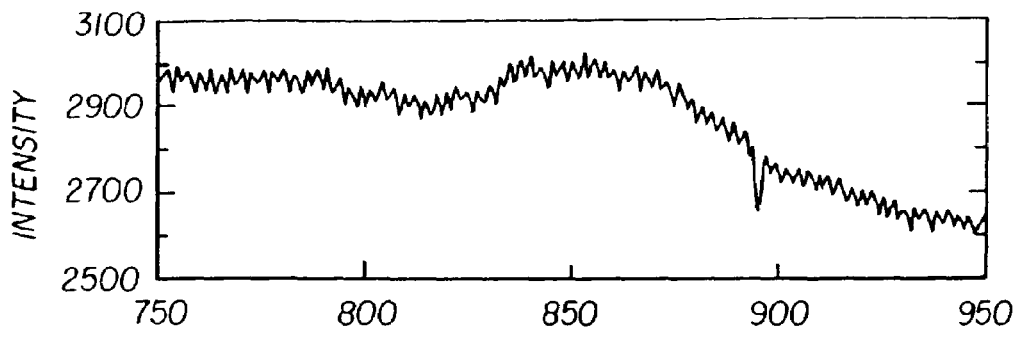
FIGS. 7A and 7B illustrate the CR image profile fragment and its corresponding Fourier spectrum with a visible grid peak.
Figure 7B:
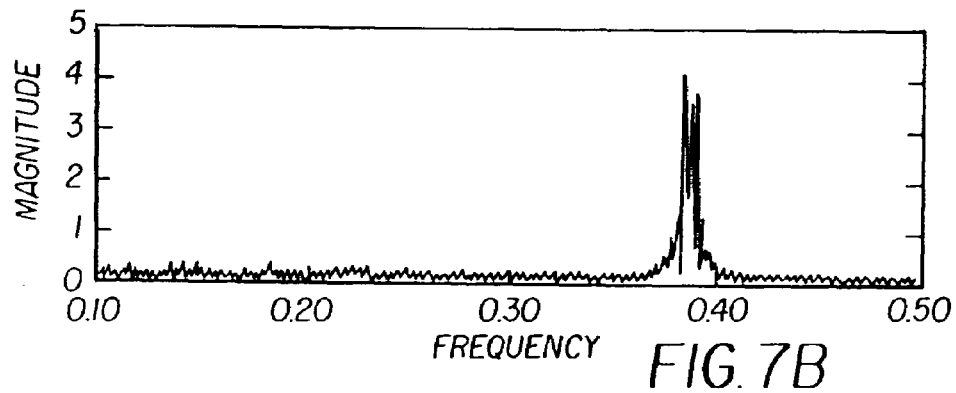

FIGS. 7A and 7B respectively illustrate the CR image profile fragment and its corresponding Fourier spectrum with a visible grid peak.

Figure 8A:
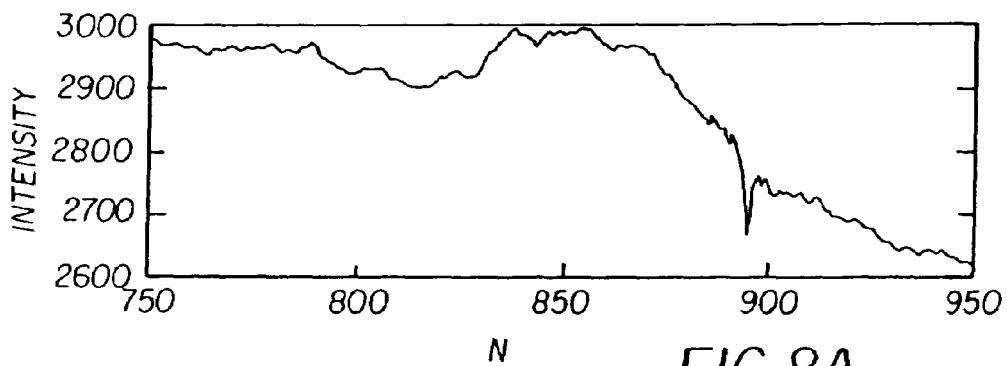
FIGS. 8A and 8B illustrate the filtered CR image profile fragment from FIG. 7 and its corresponding Fourier spectrum demonstrating the attenuation of the grid peak.
Figure 8B:
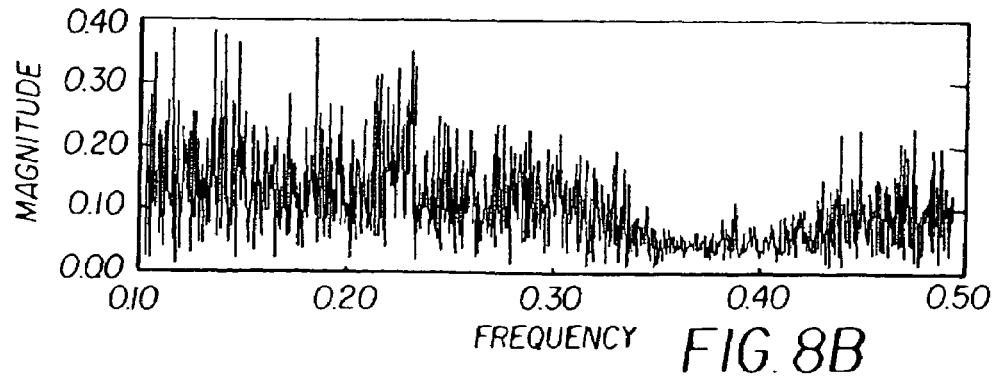

FIGS. 8A and 8B respectively illustrate the filtered CR image profile fragment of FIG. 7A and its corresponding Fourier spectrum demonstrating the attenuation of the grid peak.

The invention has been described in detail with particular reference to certain preferred embodiments thereof, but it will be understood that variations and modifications can be effected within the spirit and scope of the invention.

PARTS LIST 10 radiographic image
12 grid artifacts detector
14 grid artifacts (??) in the image
16 grid artifacts suppression
18 output digital radiographic image
20 acquisition CR/DR system or image archive
22 input image in workstation memory
24 grid artifacts detector
26 grid artifacts (??) in the image
28 output image in workstation memory
30 grid artifacts bandstop filtering
32 image display or/and archive
40 define window size and position, step, accuracy
42 input 2 horizontal or vertical image profiles
44 calculate auto correlation function
46 find spectral maximum
48 calculate cross-correlation function
50 find spectral maximum
52 equal with accuracy dF
54 $Y=N_{win}$ total number of analyzed profiles
56 calculate signal standard deviation
58 calculate SNR
60 analyze number of profiles containing grid
62 grid direction, frequency averaged SNR number
64 grid is not detected
66 output image
68 filter
70 filter design using grid frequency and SNR
72 input horizontal or vertical image profile
74 pre-convolution procedure
76 fast convolution procedure
78 post-convolution procedure
80 number of image profiles
82 output image profile
83 output image
84 input image profile
86 spike detection processing
88 profile 2 ends extension
90 fast convolution
92 fast convolution
94 image profile 2 ends cut
96 spikes recovery or removal
98 output image profile
200 x-ray source
202 object
204 image acquisition
206 digital image
208 image processor
310 memory
312 input device
314 display
316 processing unit
318 transportable storage medium drive
320 control data bus
322 output device
324 storage media

What is claimed is:

1. A method for detecting and attenuating grid artifacts in a digital radiographic image comprising:
providing an input digital radiographic image;
processing said input digital radiographic image with a detection algorithm based on 2-D dynamic correlation in both spatial and frequency domains to determine whether said input digital radiographic image has grid artifacts; and
if it does detecting the grid orientation, frequency, and signal-to-noise ratio of said grid artifacts;
designing a frequency bandstop (notch) digital 1-D filter as a function of said grid frequency and attenuation level; and
suppressing said grid artifacts by further processing said input digital radiographic image with said designed filter to produce an output digital radiographic image of improved image quality,
wherein said processing includes consequent dynamic analyzing image profiles in two dimensions both in spatial and in frequency domains in a predefined square sub-region of the input digital radiographic image (window) in each of horizontal and vertical directions, and
wherein said consequent dynamic analyzing includes calculating and analyzing auto-correlation (ACF) and cross-correlation (CCF) functions for 2 image profiles with predefined incremental step in said predefined window.

2. The method of claim 1 wherein said analyzing of ACF and CCF includes:
obtaining Fourier power spectra of ACF and CCF $1^{st}$ derivatives;
averaging the obtained Fourier power spectra;
searching for the frequencies of the maxima in the right part of averaged Fourier spectra; and
checking that these frequencies of the maxima are the same values, within predefined accuracy.

3. The method of claim 2 wherein said dynamic analyzing includes tracking successful matches of found frequency values treated as detected grid artifacts.

4. The method of claim 2 wherein said detecting of grid frequency includes detecting a grid frequency and maximum magnitude in a current image profile Fourier spectrum within the bandwidth equal to the pre-defined accuracy at the found frequency for CCF.

5. The method of claim 2 wherein said detecting of grid signal-to-noise (SNR) ratio includes:
calculating a standard deviation of signal frequencies within the bandwidth equal to the predefined accuracy at the frequency of 0.25 of Nyquist;
calculating and accumulating current image profile SNR as a ratio of said standard deviation and said grid maximum magnitude; and
calculating SNR averaged by total number of profiles with detected grid artifacts.

6. The method of claim 2 wherein said detecting of grid frequency includes calculating the grid frequency from the frequencies of the maxima found in the right part of the CCF $1^{st}$ derivative power spectrum, averaged over all image profiles that contain detected grid artifacts.

7. The method of claim 1 wherein said designing includes calculating finite impulse response notch filter coefficients, wherein said finite impulse response notch filter coefficients calculating includes using a trigonometric trapezoid filter algorithm with Potter P310 smoothing window; and
wherein said step of suppressing includes using a spike effect elimination function and an edge effect elimination function.

8. A method for detecting and attenuating grid artifacts in a digital radiographic image comprising:
providing an input digital radiographic image;
processing said input digital radiographic image with a detection algorithm based on 2-D dynamic correlation in both spatial and frequency domains to determine whether said input digital radiographic image has grid artifacts; and if it does detecting the grid orientation, frequency, and signal-to-noise ratio of said grid artifacts;

designing a frequency bandstop (notch) digital 1-D filter as a function of said grid frequency and attenuation level; and suppressing said grid artifacts by further processing said input digital radiographic image with said designed filter to produce an output digital radiographic image of improved image quality;

wherein said suppressing includes a pre-convolution procedure, a fast convolution procedure, and a post-convolution procedure;

wherein said pre-convolution and post-convolution procedures include using a spike effect elimination function and an edge effect elimination function; and wherein said spike effect elimination function includes using a spike detection algorithm comprising the steps of:

retaining spike locations and values until convolution is completed;

substituting spike values with linear interpolated neighbor values; and optionally replacing the spike values to their origin locations after convolution.

9. A method for detecting and attenuating grid artifacts in a digital radiographic image comprising:

providing an input digital radiographic image;

processing said input digital radiographic image with a detection algorithm based on 2-D dynamic correlation in both spatial and frequency domains to determine whether said input digital radiographic image has grid artifacts; and if it does detecting the grid orientation, frequency, and signal-to-noise ratio of said grid artifacts;

designing a frequency bandstop (notch) digital 1-D filter as a function of said grid frequency and attenuation level; and suppressing said grid artifacts by further processing said input digital radiographic image with said designed filter to produce an output digital radiographic image of improved image quality;

wherein said suppressing includes a pre-convolution procedure, a fast convolution procedure, and a post-convolution procedure;

wherein said pre-convolution and post-convolution procedures include using a spike effect elimination function and an edge effect elimination function; and wherein said edge effect elimination function includes the steps of:

extending said image profile at both the ends to filter operator length by replicating first and last values at each end before said convolution; and removing the extended image profile after said convolution.

* * * * *